US012678133B2

(12) United States Patent (10) Patent No.: US 12,678,133 B2
Misener et al. (45) Date of Patent: *Jul. 14, 2026

(54) ULTRASOUND PROBE WITH SMART ACCESSORY

(71) Applicant: Bard Access Systems, Inc., Salt Lake City, UT (US)

(72) Inventors: Anthony K. Misener, Bountiful, UT (US); Steffan Sowards, Salt Lake City, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/885,090

(22) Filed: Sep. 13, 2024

(65) Prior Publication Data

US 2025/0000488 A1 Jan. 2, 2025

Related U.S. Application Data

(63) Continuation of application No. 17/832,389, filed on Jun. 3, 2022, now Pat. No. 12,102,481.

(51) Int. Cl.
*A61B 8/00* (2006.01)
(52) U.S. Cl.
CPC .......... *A61B 8/4444* (2013.01); *A61B 8/4411* (2013.01); *A61B 8/462* (2013.01); *A61B 8/56* (2013.01)
(58) Field of Classification Search
CPC ..... A61B 8/4444; A61B 8/4411; A61B 8/462; A61B 8/56
See application file for complete search history.

(56) References Cited

U.S. PATENT DOCUMENTS

| 4,311,138 | A | 1/1982 | Sugarman |
| 4,971,068 | A | 11/1990 | Sahi |

(Continued)

FOREIGN PATENT DOCUMENTS

| AU | 2006201646 A1 | 11/2006 |
| CN | 114129137 B | 9/2022 |

(Continued)

OTHER PUBLICATIONS

EZono, eZSimulator, https://www.ezono.com/en/ezsimulator/, last accessed Sep. 13, 2022.

(Continued)

*Primary Examiner* — Alexei Bykhovski
(74) *Attorney, Agent, or Firm* — Rutan & Tucker LLP

(57) ABSTRACT

A medical ultrasound system and methods of using the system. The medical ultrasound system can include an ultrasound probe and one of a plurality of optional accessories attached to the ultrasound probe. The accessory can exchange data with the probe and receive power from the probe. The accessory can include processors and logic that governs its operation thereby adding functionality to the probe. The accessory can receive input and provide output via any of a number of communication mechanisms, i.e., wireless, electrical, optical, RFID, IR, and the like. The accessory can add functionality to the probe, such as fiber optic shape sensing, obtaining electrical signals, obtaining bio-impedance measurements, tracking a needle, and determining the orientation of the probe. The accessory may include a needle guide, a triphalangeal support structure, or an acoustically transparent cap.

17 Claims, 5 Drawing Sheets

(56) References Cited

U.S. PATENT DOCUMENTS

| | | | |
|---|---|---|---|
| 5,148,809 A | 9/1992 | Biegeleisen-Knight et al. |
| 5,181,513 A | 1/1993 | Touboul et al. |
| 5,325,293 A | 6/1994 | Dorne |
| 5,441,052 A | 8/1995 | Miyajima |
| 5,549,554 A | 8/1996 | Miraki |
| 5,573,529 A | 11/1996 | Haak et al. |
| 5,775,322 A | 7/1998 | Silverstein et al. |
| 5,879,297 A | 3/1999 | Haynor et al. |
| 5,908,387 A | 6/1999 | LeFree et al. |
| 5,967,984 A | 10/1999 | Chu et al. |
| 5,970,119 A | 10/1999 | Hofmann |
| 6,004,270 A | 12/1999 | Urbano et al. |
| 6,019,724 A | 2/2000 | Gronningsaeter et al. |
| 6,068,599 A | 5/2000 | Saito et al. |
| 6,074,367 A | 6/2000 | Hubbell |
| 6,129,668 A | 10/2000 | Haynor et al. |
| 6,132,379 A | 10/2000 | Patacsil et al. |
| 6,216,028 B1 | 4/2001 | Haynor et al. |
| 6,233,476 B1 | 5/2001 | Strommer et al. |
| 6,245,018 B1 | 6/2001 | Lee |
| 6,263,230 B1 | 7/2001 | Haynor et al. |
| 6,375,615 B1 | 4/2002 | Flaherty et al. |
| 6,436,043 B2 | 8/2002 | Bonnefous |
| 6,498,942 B1 | 12/2002 | Esenaliev et al. |
| 6,503,205 B2 | 1/2003 | Manor et al. |
| 6,508,769 B2 | 1/2003 | Bonnefous |
| 6,511,458 B2 | 1/2003 | Milo et al. |
| 6,524,249 B2 | 2/2003 | Moehring et al. |
| 6,543,642 B1 | 4/2003 | Milliorn |
| 6,554,771 B1 | 4/2003 | Buil et al. |
| 6,592,520 B1 | 7/2003 | Peszynski et al. |
| 6,592,565 B2 | 7/2003 | Twardowski |
| 6,601,705 B2 | 8/2003 | Molina et al. |
| 6,612,992 B1 | 9/2003 | Hossack et al. |
| 6,613,002 B1 | 9/2003 | Clark et al. |
| 6,623,431 B1 | 9/2003 | Sakuma et al. |
| 6,641,538 B2 | 11/2003 | Nakaya et al. |
| 6,647,135 B2 | 11/2003 | Bonnefous |
| 6,687,386 B1 | 2/2004 | Ito et al. |
| 6,749,569 B1 | 6/2004 | Pellegretti |
| 6,754,608 B2 | 6/2004 | Svanerudh et al. |
| 6,755,789 B2 | 6/2004 | Stringer et al. |
| 6,840,379 B2 | 1/2005 | Franks-Farah et al. |
| 6,857,196 B2 | 2/2005 | Dalrymple |
| 6,979,294 B1 | 12/2005 | Selzer et al. |
| 7,074,187 B2 | 7/2006 | Selzer et al. |
| 7,244,234 B2 | 7/2007 | Ridley et al. |
| 7,359,554 B2 | 4/2008 | Klingensmith et al. |
| 7,534,209 B2 | 5/2009 | Abend et al. |
| 7,599,730 B2 | 10/2009 | Hunter et al. |
| 7,637,870 B2 | 12/2009 | Flaherty et al. |
| 7,681,579 B2 | 3/2010 | Schwartz |
| 7,691,061 B2 | 4/2010 | Hirota |
| 7,699,779 B2 | 4/2010 | Sasaki et al. |
| 7,720,520 B2 | 5/2010 | Willis |
| 7,727,153 B2 | 6/2010 | Fritz et al. |
| 7,734,326 B2 | 6/2010 | Pedain et al. |
| 7,831,449 B2 | 11/2010 | Mng et al. |
| 7,905,837 B2 | 3/2011 | Suzuki |
| 7,925,327 B2 | 4/2011 | Weese |
| 7,927,278 B2 | 4/2011 | Selzer et al. |
| 8,014,848 B2 | 9/2011 | Birkenbach et al. |
| 8,050,523 B2 | 11/2011 | Younge et al. |
| 8,060,181 B2 | 11/2011 | Rodriguez Ponce et al. |
| 8,068,581 B2 | 11/2011 | Boese et al. |
| 8,075,488 B2 | 12/2011 | Burton |
| 8,090,427 B2 | 1/2012 | Eck et al. |
| 8,105,239 B2 | 1/2012 | Specht |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,211,023 B2 | 7/2012 | Swan et al. |
| 8,228,347 B2 | 7/2012 | Beasley et al. |
| 8,298,147 B2 | 10/2012 | Huennekens et al. |
| 8,303,505 B2 | 11/2012 | Webler et al. |
| 8,323,202 B2 | 12/2012 | Roschak et al. |
| 8,328,727 B2 | 12/2012 | Miele et al. |
| 8,388,541 B2 | 3/2013 | Messerly et al. |
| 8,409,103 B2 | 4/2013 | Grunwald et al. |
| 8,449,465 B2 | 5/2013 | Nair et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,622,913 B2 | 1/2014 | Dentinger et al. |
| 8,706,457 B2 | 4/2014 | Hart et al. |
| 8,727,988 B2 | 5/2014 | Flaherty et al. |
| 8,734,357 B2 | 5/2014 | Taylor |
| 8,744,211 B2 | 6/2014 | Owen |
| 8,754,865 B2 | 6/2014 | Merritt et al. |
| 8,764,663 B2 | 7/2014 | Smok et al. |
| 8,781,194 B2 | 7/2014 | Malek et al. |
| 8,781,555 B2 | 7/2014 | Burnside et al. |
| 8,790,263 B2 | 7/2014 | Randall et al. |
| 8,849,382 B2 | 9/2014 | Cox et al. |
| 8,939,908 B2 | 1/2015 | Suzuki et al. |
| 8,961,420 B2 | 2/2015 | Zhang |
| 9,022,940 B2 | 5/2015 | Meier |
| 9,138,290 B2 | 9/2015 | Hadjicostis |
| 9,155,517 B2 | 10/2015 | Dunbar et al. |
| 9,204,858 B2 | 12/2015 | Pelissier et al. |
| 9,220,477 B2 | 12/2015 | Urabe et al. |
| 9,257,220 B2 | 2/2016 | Nicholls et al. |
| 9,295,447 B2 | 3/2016 | Shah |
| 9,320,493 B2 | 4/2016 | Visveshwara |
| 9,357,980 B2 | 6/2016 | Toji et al. |
| 9,364,171 B2 | 6/2016 | Harris et al. |
| 9,427,207 B2 | 8/2016 | Sheldon et al. |
| 9,445,780 B2 | 9/2016 | Hossack et al. |
| 9,456,766 B2 | 10/2016 | Cox et al. |
| 9,456,804 B2 | 10/2016 | Tamada |
| 9,459,087 B2 | 10/2016 | Dunbar et al. |
| 9,468,413 B2 | 10/2016 | Hall et al. |
| 9,492,097 B2 | 11/2016 | Wilkes et al. |
| 9,521,961 B2 | 12/2016 | Silverstein et al. |
| 9,554,716 B2 | 1/2017 | Burnside et al. |
| 9,582,876 B2 | 2/2017 | Specht |
| 9,597,008 B2 | 3/2017 | Henkel et al. |
| 9,610,061 B2 | 4/2017 | Ebbini et al. |
| 9,636,031 B2 | 5/2017 | Cox |
| 9,649,037 B2 | 5/2017 | Lowe et al. |
| 9,649,048 B2 | 5/2017 | Cox et al. |
| 9,702,969 B2 | 7/2017 | Hope Simpson et al. |
| 9,715,757 B2 | 7/2017 | Ng et al. |
| 9,717,415 B2 | 8/2017 | Cohen et al. |
| 9,731,066 B2 | 8/2017 | Liu et al. |
| 9,814,433 B2 | 11/2017 | Benishti et al. |
| 9,814,531 B2 | 11/2017 | Yagi et al. |
| 9,861,337 B2 | 1/2018 | Patwardhan et al. |
| 9,895,138 B2 | 2/2018 | Sasaki |
| 9,913,605 B2 | 3/2018 | Harris et al. |
| 9,949,720 B2 | 4/2018 | Southard et al. |
| 10,010,379 B1 | 7/2018 | Gibby et al. |
| 10,043,272 B2 | 8/2018 | Forzoni et al. |
| 10,380,919 B2 | 8/2019 | Savitsky et al. |
| 10,380,920 B2 | 8/2019 | Savitsky et al. |
| 10,424,225 B2 | 9/2019 | Nataneli et al. |
| 10,434,278 B2 | 10/2019 | Dunbar et al. |
| 10,449,330 B2 | 10/2019 | Newman et al. |
| 10,524,691 B2 | 1/2020 | Newman et al. |
| 10,636,323 B2 | 4/2020 | Buras et al. |
| 10,674,935 B2 | 6/2020 | Henkel et al. |
| 10,751,509 B2 | 8/2020 | Misener |
| 10,758,155 B2 | 9/2020 | Henkel et al. |
| 10,765,343 B2 | 9/2020 | Henkel et al. |
| 10,796,605 B2 | 10/2020 | Buras et al. |
| 10,818,199 B2 | 10/2020 | Buras et al. |
| 10,835,207 B2 | 11/2020 | Altmann et al. |
| 10,869,727 B2 | 12/2020 | Yanof et al. |
| 10,896,628 B2 | 1/2021 | Savitsky et al. |
| 11,011,078 B2 | 5/2021 | Buras et al. |
| 11,017,694 B2 | 5/2021 | Buras et al. |
| 11,017,695 B2 | 5/2021 | Buras et al. |
| 11,062,624 B2 | 7/2021 | Savitsky et al. |
| 11,120,709 B2 | 9/2021 | Savitsky et al. |

(56) References Cited

U.S. PATENT DOCUMENTS

| | | |
|---|---|---|
| 11,311,269 B2 | 4/2022 | Dunbar et al. |
| 11,315,439 B2 | 4/2022 | Savitsky et al. |
| 11,495,142 B2 | 11/2022 | Petrinec et al. |
| 11,600,201 B1 | 3/2023 | Savitsky et al. |
| 11,676,513 B2 | 6/2023 | Buras et al. |
| 12,062,297 B2 | 8/2024 | Buras et al. |
| 12,144,675 B2 | 11/2024 | Durfee |
| 12,396,656 B2 | 8/2025 | Durfee et al. |
| 12,414,835 B2 | 9/2025 | Gibby et al. |
| 2002/0038088 A1 | 3/2002 | Imran et al. |
| 2002/0148277 A1 | 10/2002 | Umeda |
| 2003/0028112 A1 | 2/2003 | Paladini et al. |
| 2003/0047126 A1 | 3/2003 | Tomaschko |
| 2003/0060714 A1 | 3/2003 | Henderson et al. |
| 2003/0073900 A1 | 4/2003 | Senarith et al. |
| 2003/0093001 A1 | 5/2003 | Martikainen |
| 2003/0106825 A1 | 6/2003 | Molina et al. |
| 2003/0120154 A1 | 6/2003 | Sauer et al. |
| 2003/0226868 A1 | 12/2003 | Monden |
| 2004/0055925 A1 | 3/2004 | Franks-Farah et al. |
| 2005/0000975 A1 | 1/2005 | Carco et al. |
| 2005/0049504 A1 | 3/2005 | Lo et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0013523 A1 | 1/2006 | Childlers et al. |
| 2006/0015039 A1 | 1/2006 | Cassidy et al. |
| 2006/0020204 A1 | 1/2006 | Serra et al. |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0199848 A1 | 8/2007 | Ellswood et al. |
| 2007/0239120 A1 | 10/2007 | Brock et al. |
| 2007/0249911 A1 | 10/2007 | Simon |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0255475 A1 | 10/2008 | Kondrosky et al. |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0306509 A1 | 12/2009 | Pedersen et al. |
| 2010/0004539 A1 | 1/2010 | Chen et al. |
| 2010/0020926 A1 | 1/2010 | Boese et al. |
| 2010/0106015 A1 | 4/2010 | Norris |
| 2010/0160786 A1 | 6/2010 | Nordgren et al. |
| 2010/0179428 A1 | 7/2010 | Pedersen et al. |
| 2010/0211026 A2 | 8/2010 | Sheetz et al. |
| 2010/0277305 A1 | 11/2010 | Garner et al. |
| 2010/0286515 A1 | 11/2010 | Gravenstein et al. |
| 2010/0312121 A1 | 12/2010 | Guan |
| 2011/0002518 A1 | 1/2011 | Ziv-Ari et al. |
| 2011/0071404 A1 | 3/2011 | Schmitt et al. |
| 2011/0166451 A1 | 7/2011 | Blaivas et al. |
| 2011/0288405 A1 | 11/2011 | Razavi et al. |
| 2011/0295108 A1 | 12/2011 | Cox et al. |
| 2011/0313293 A1 | 12/2011 | Lindekugel et al. |
| 2012/0136242 A1 | 5/2012 | Qi et al. |
| 2012/0179038 A1 | 7/2012 | Meurer et al. |
| 2012/0197132 A1 | 8/2012 | O'Connor |
| 2012/0209121 A1 | 8/2012 | Boudier |
| 2012/0220865 A1 | 8/2012 | Brown et al. |
| 2012/0238875 A1 | 9/2012 | Savitsky et al. |
| 2012/0277576 A1 | 11/2012 | Lui |
| 2013/0041250 A1 | 2/2013 | Pelissier et al. |
| 2013/0102889 A1 | 4/2013 | Southard et al. |
| 2013/0131499 A1 | 5/2013 | Chan et al. |
| 2013/0131502 A1 | 5/2013 | Blaivas et al. |
| 2013/0150724 A1 | 6/2013 | Blaivas et al. |
| 2013/0188832 A1 | 7/2013 | Ma et al. |
| 2013/0218024 A1 | 8/2013 | Boctor et al. |
| 2013/0296651 A1 | 11/2013 | Ito et al. |
| 2013/0324840 A1 | 12/2013 | Zhongping et al. |
| 2014/0005530 A1 | 1/2014 | Liu et al. |
| 2014/0031690 A1 | 1/2014 | Toji et al. |
| 2014/0036091 A1 | 2/2014 | Zalev et al. |
| 2014/0073976 A1 | 3/2014 | Fonte et al. |
| 2014/0100440 A1 | 4/2014 | Cheline et al. |
| 2014/0155737 A1 | 6/2014 | Manzke et al. |
| 2014/0180098 A1 | 6/2014 | Flaherty et al. |
| 2014/0187920 A1 | 7/2014 | Millett et al. |
| 2014/0188133 A1 | 7/2014 | Misener |
| 2014/0188440 A1 | 7/2014 | Donhowe et al. |
| 2014/0257104 A1 | 9/2014 | Dunbar et al. |
| 2014/0276059 A1 | 9/2014 | Sheehan |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0157295 A1 | 6/2015 | Liu et al. |
| 2015/0209113 A1 | 7/2015 | Burkholz et al. |
| 2015/0209526 A1 | 7/2015 | Matsubara et al. |
| 2015/0294497 A1 | 10/2015 | Ng et al. |
| 2015/0297097 A1 | 10/2015 | Matsubara et al. |
| 2015/0305718 A1 | 10/2015 | Ogasawara |
| 2015/0327841 A1 | 11/2015 | Banjanin et al. |
| 2015/0359991 A1 | 12/2015 | Dunbar et al. |
| 2016/0029995 A1 | 2/2016 | Navratil et al. |
| 2016/0029998 A1 | 2/2016 | Brister et al. |
| 2016/0058420 A1 | 3/2016 | Cinthio et al. |
| 2016/0074015 A1 | 3/2016 | Eda |
| 2016/0100970 A1 | 4/2016 | Brister et al. |
| 2016/0101263 A1 | 4/2016 | Blumenkranz et al. |
| 2016/0113699 A1 | 4/2016 | Sverdlik et al. |
| 2016/0120607 A1 | 5/2016 | Sorotzkin et al. |
| 2016/0143622 A1 | 5/2016 | Xie et al. |
| 2016/0157808 A1 | 6/2016 | Merritt et al. |
| 2016/0166232 A1 | 6/2016 | Merritt |
| 2016/0202053 A1 | 7/2016 | Walker et al. |
| 2016/0213398 A1 | 7/2016 | Liu |
| 2016/0278743 A1 | 9/2016 | Kawashima |
| 2016/0278869 A1 | 9/2016 | Grunwald |
| 2016/0296208 A1 | 10/2016 | Sethuraman et al. |
| 2016/0374644 A1 | 12/2016 | Mauldin, Jr. et al. |
| 2017/0056062 A1 | 3/2017 | Buljubasic |
| 2017/0079548 A1 | 3/2017 | Silverstein et al. |
| 2017/0086785 A1 | 3/2017 | Bjaerum |
| 2017/0100092 A1 | 4/2017 | Kruse et al. |
| 2017/0164923 A1 | 6/2017 | Matsumoto |
| 2017/0172424 A1 | 6/2017 | Eggers et al. |
| 2017/0188839 A1 | 7/2017 | Tashiro |
| 2017/0196535 A1 | 7/2017 | Arai et al. |
| 2017/0215842 A1 | 8/2017 | Ryu et al. |
| 2017/0252002 A1 | 9/2017 | Mine et al. |
| 2017/0259013 A1 | 9/2017 | Boyden et al. |
| 2017/0265840 A1 | 9/2017 | Bharat et al. |
| 2017/0303894 A1 | 10/2017 | Scully |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0220993 A1 | 8/2018 | Poland |
| 2018/0225993 A1 | 8/2018 | Buras et al. |
| 2018/0228465 A1 | 8/2018 | Southard et al. |
| 2018/0235576 A1 | 8/2018 | Brannan |
| 2018/0250078 A1 | 9/2018 | Shochat et al. |

(56) References Cited

U.S. PATENT DOCUMENTS

| | | |
|---|---|---|
| 2018/0272108 A1 | 9/2018 | Padilla et al. |
| 2018/0279996 A1 | 10/2018 | Cox et al. |
| 2018/0286287 A1 | 10/2018 | Razzaque |
| 2018/0310955 A1 | 11/2018 | Lindekugel et al. |
| 2018/0317881 A1 | 11/2018 | Astigarraga et al. |
| 2018/0366035 A1 | 12/2018 | Dunbar et al. |
| 2019/0060014 A1 | 2/2019 | Hazelton et al. |
| 2019/0069923 A1 | 3/2019 | Wang |
| 2019/0076121 A1 | 3/2019 | Southard et al. |
| 2019/0088019 A1 | 3/2019 | Prevrhal et al. |
| 2019/0105017 A1 | 4/2019 | Hastings |
| 2019/0117190 A1 | 4/2019 | Djajadiningrat et al. |
| 2019/0167148 A1 | 6/2019 | Durfee et al. |
| 2019/0223757 A1 | 7/2019 | Durfee |
| 2019/0223958 A1 | 7/2019 | Kohli et al. |
| 2019/0239850 A1 | 8/2019 | Dalvin et al. |
| 2019/0282262 A1 | 9/2019 | Bouazza-Marouf et al. |
| 2019/0282324 A1 | 9/2019 | Freeman et al. |
| 2019/0298457 A1 | 10/2019 | Bharat |
| 2019/0307419 A1 | 10/2019 | Durfee |
| 2019/0307516 A1 | 10/2019 | Schotzko et al. |
| 2019/0339525 A1 | 11/2019 | Yanof et al. |
| 2019/0355278 A1 | 11/2019 | Sainsbury et al. |
| 2019/0365348 A1 | 12/2019 | Toume et al. |
| 2020/0041261 A1 | 2/2020 | Bernstein et al. |
| 2020/0069285 A1 | 3/2020 | Annangi et al. |
| 2020/0069929 A1 | 3/2020 | Mason et al. |
| 2020/0113540 A1 | 4/2020 | Gijsbers et al. |
| 2020/0129136 A1 | 4/2020 | Harding et al. |
| 2020/0188028 A1 | 6/2020 | Feiner et al. |
| 2020/0230391 A1 | 7/2020 | Burkholz et al. |
| 2020/0305927 A1 | 10/2020 | Grim et al. |
| 2020/0367860 A1 | 11/2020 | Rouet et al. |
| 2021/0007710 A1 | 1/2021 | Douglas |
| 2021/0045716 A1 | 2/2021 | Shiran et al. |
| 2021/0161612 A1 | 6/2021 | Black et al. |
| 2021/0166583 A1 | 6/2021 | Buras et al. |
| 2021/0307838 A1 | 10/2021 | Xia et al. |
| 2021/0327303 A1 | 10/2021 | Buras et al. |
| 2021/0353255 A1 | 11/2021 | Schneider et al. |
| 2021/0402144 A1 | 12/2021 | Messerly |
| 2022/0022969 A1 | 1/2022 | Misener |
| 2022/0031965 A1 | 2/2022 | Durfee |
| 2022/0039685 A1 | 2/2022 | Misener et al. |
| 2022/0039777 A1 | 2/2022 | Durfee |
| 2022/0054108 A1 | 2/2022 | In 'T Groen et al. |
| 2022/0096797 A1 | 3/2022 | Prince |
| 2022/0104886 A1 | 4/2022 | Blanchard et al. |
| 2022/0117582 A1 | 4/2022 | Mclaughlin et al. |
| 2022/0160434 A1 | 5/2022 | Messerly et al. |
| 2022/0168050 A1 | 6/2022 | Sowards et al. |
| 2022/0172354 A1 | 6/2022 | Misener et al. |
| 2022/0211442 A1 | 7/2022 | Mclaughlin et al. |
| 2022/0354462 A1 | 11/2022 | Southworth et al. |
| 2022/0381630 A1 | 12/2022 | Sowards et al. |
| 2022/0401157 A1 | 12/2022 | Sowards et al. |
| 2023/0053189 A1 | 2/2023 | Geric et al. |
| 2023/0113291 A1 | 4/2023 | de Wild et al. |
| 2023/0240643 A1 | 8/2023 | Cermak et al. |
| 2023/0389893 A1 | 12/2023 | Misener et al. |
| 2024/0008929 A1 | 1/2024 | Misener et al. |
| 2024/0050060 A1 | 2/2024 | Kadokura et al. |
| 2024/0050061 A1 | 2/2024 | McLaughlin et al. |
| 2024/0058074 A1 | 2/2024 | Misener |
| 2024/0062678 A1 | 2/2024 | Sowards et al. |
| 2025/0032152 A1 | 1/2025 | Miller et al. |
| 2025/0057604 A1 | 2/2025 | Blanchard et al. |
| 2025/0064425 A1 | 2/2025 | Durfee |
| 2025/0143804 A1 | 5/2025 | Misener |
| 2025/0176942 A1 | 6/2025 | McLaughlin et al. |
| 2025/0339174 A1 | 11/2025 | Durfee et al. |

FOREIGN PATENT DOCUMENTS

| | | | |
|---|---|---|---|
| EP | 0933063 | A1 | 8/1999 |
| EP | 1504713 | A1 | 2/2005 |
| EP | 1591074 | B1 | 5/2008 |
| EP | 3181083 | A1 | 6/2017 |
| EP | 3530221 | A1 | 8/2019 |
| JP | 2000271136 | A | 10/2000 |
| JP | 2014150928 | A | 8/2014 |
| JP | 2018175547 | A | 11/2018 |
| KR | 20180070878 | A | 6/2018 |
| KR | 20190013133 | A | 2/2019 |
| KR | 20220141308 | A | 10/2022 |
| WO | 2013059714 | A1 | 4/2013 |
| WO | 2014115150 | A1 | 7/2014 |
| WO | 2014174305 | A2 | 10/2014 |
| WO | 2015017270 | A1 | 2/2015 |
| WO | 2017096487 | A1 | 6/2017 |
| WO | 2017214428 | A1 | 12/2017 |
| WO | 2018026878 | A1 | 2/2018 |
| WO | 2018134726 | A1 | 7/2018 |
| WO | 2018206473 | A1 | 11/2018 |
| WO | 2019232451 | A1 | 12/2019 |
| WO | 2020002620 | A1 | 1/2020 |
| WO | 2020016018 | A1 | 1/2020 |
| WO | 2019232454 | A9 | 2/2020 |
| WO | 2020044769 | A1 | 3/2020 |
| WO | 2020102665 | A1 | 5/2020 |
| WO | 2020186198 | A1 | 9/2020 |
| WO | 2022031762 | A1 | 2/2022 |
| WO | 2022072727 | A2 | 4/2022 |
| WO | 2022081904 | A1 | 4/2022 |
| WO | 2022203713 | A2 | 9/2022 |
| WO | 2022263763 | A1 | 12/2022 |
| WO | 2023235435 | A1 | 12/2023 |
| WO | 2024010940 | A1 | 1/2024 |
| WO | 2024039608 | A1 | 2/2024 |
| WO | 2024039719 | A1 | 2/2024 |
| WO | 2025024821 | A1 | 1/2025 |
| WO | 2025231303 | A1 | 11/2025 |

OTHER PUBLICATIONS

Ikhsan Mohammad et al.: "Assistive technology for ultrasound-guided central venous catheter placement", Journal of Medical Ultrasonics, Japan Society of Ultrasonics in Medicine, Tokyo, JP, vol. 45, No. 1, Apr. 19, 2017, pp. 41-57, XPO36387340, ISSN: 1346-4523, DOI: 10.1007/S10396-017-0789-2 [retrieved on Apr. 19, 2017].

Lu Zhenyu et al."Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).

Pagoulatos, N. et al. "New spatial localizer based on fiber optics with applications in 3D ultrasound imaging" Proceeding of Spie, vol. 3976 (Apr. 18, 2000; Apr. 18, 2000).

PCT/US2021/042369 filed Jul. 20, 2021 International Search Report and Written Opinion dated Oct. 25, 2021.

PCT/US2021/044419 filed Aug. 3, 2021 International Search Report and Written Opinion dated Nov. 19, 2021.

PCT/US2021/045218 filed Aug. 9, 2021 International Search Report and Written Opinion dated Nov. 23, 2021.

PCT/US2021/050973 filed Sep. 17, 2021 International Search Report and Written Opinion dated Nov. 7, 2022.

PCT/US2021/053018 filed Sep. 30, 2021 International Search Report and Written Opinion dated May 3, 2022.

PCT/US2021/055076 filed Oct. 14, 2021 International Search Report and Written Opinion dated Mar. 25, 2022.

PCT/US2023/024067 filed May 31, 2023 International Search Report and Written Opinion dated Sep. 15, 2023.

PCT/US2023/027147 filed Jul. 7, 2023 International Search Report and Written Opinion dated Oct. 2, 2023.

PCT/US2023/030160 filed Aug. 14, 2023 International Search Report and Written Opinion dated Oct. 23, 2023.

(56) References Cited

OTHER PUBLICATIONS

PCT/US2023/030347 filed Aug. 16, 2023 International Search Report and Written Opinion dated Nov. 6, 2023.

Practical guide for safe central venous catheterization and management 2017 Journal of Anesthesia vol. 34 published online Nov. 30, 2019 pp. 167-186.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docld/1235/file/Sebastian VogtDissertation.pdf.

Sonosim, https://sonosim.com/ultrasound-simulation/? last accessed Sep. 13, 2022.

State, A., et al. (1996, August). Technologies for augmented reality systems: Realizing ultrasound-guided needle biopsies. In Proceedings of the 23rd annual conference on computer graphics and interactive techniques (pp. 439-446) (Year: 1996).

Stolka, P.J., et al., (2014). Needle Guidance Using Handheld Stereo Vision and Projection for Ultrasound-Based Interventions. In: Galland, P., Hata, N., Barillot, C., Hornegger, J., Howe, R. (eds) Medical Image Computing and Computer-Assisted Intervention—MICCAI 2014. MICCAI 2014. (Year: 2014).

U.S. Appl. No. 17/380,767, filed Jul. 20, 2021 Non-Final Office Action dated Mar. 6, 2023.

U.S. Appl. No. 17/380,767, filed Jul. 20, 2021 Notice of Allowance dated Aug. 31, 2023.

U.S. Appl. No. 17/380,767, filed Jul. 20, 2021 Restriction Requirement dated Dec. 15, 2022.

U.S. Appl. No. 17/393,283, filed Aug. 3, 2021 Advisory Action dated Jan. 19, 2024.

U.S. Appl. No. 17/393,283, filed Aug. 3, 2021 Final Office Action dated Oct. 16, 2023.

U.S. Appl. No. 17/393,283, filed Aug. 3, 2021 Non-Final Office Action dated Feb. 29, 2024.

U.S. Appl. No. 17/393,283, filed Aug. 3, 2021 Non-Final Office Action dated Mar. 31, 2023.

U.S. Appl. No. 17/393,283, filed Aug. 3, 2021 Notice of Allowance dated Sep. 18, 2024.

U.S. Appl. No. 17/393,283, filed Aug. 3, 2021 Restriction Requirement dated Jan. 12, 2023.

U.S. Appl. No. 17/397,486, filed Aug. 9, 2021 Advisory Action dated Oct. 5, 2023.

U.S. Appl. No. 17/397,486, filed Aug. 9, 2021 Final Office Action dated Aug. 4, 2023.

U.S. Appl. No. 17/397,486, filed Aug. 9, 2021 Non-Final Office Action dated Jan. 23, 2023.

U.S. Appl. No. 17/397,486, filed Aug. 9, 2021 Non-Final Office Action dated Mar. 1, 2024.

U.S. Appl. No. 17/397,486, filed Aug. 9, 2021 Notice of Allowance dated Jul. 10, 2024.

U.S. Appl. No. 17/397,486, filed Aug. 9, 2021 Restriction Requirement dated Aug. 12, 2022.

U.S. Appl. No. 17/478,754, filed Sep. 17, 2021 Non-Final Office Action dated Jul. 1, 2024.

U.S. Appl. No. 17/478,754, filed Sep. 17, 2021 Restriction Requirement dated Jan. 22, 2024.

U.S. Appl. No. 17/491,308, filed Sep. 30, 2021 Board Decision dated Oct. 25, 2023.

U.S. Appl. No. 17/491,308, filed Sep. 30, 2021 Board Decison dated Oct. 25, 2023.

U.S. Appl. No. 17/491,308, filed Sep. 30, 2021 Final Office Action dated Aug. 29, 2023.

U.S. Appl. No. 17/491,308, filed Sep. 30, 2021 Non-Final Office Action dated Jun. 5, 2023.

U.S. Appl. No. 17/491,308, filed Sep. 30, 2021 Non-Final Office Action dated Mar. 22, 2024.

U.S. Appl. No. 17/491,308, filed Sep. 30, 2021 Notice of Allowance dated Jun. 27, 2024.

U.S. Appl. No. 17/491,308, filed Sep. 30, 2021 Restriction Requirement dated Feb. 27, 2023.

U.S. Appl. No. 17/501,909, filed Oct. 14, 2021 Advisory Action dated Jan. 24, 2024.

U.S. Appl. No. 17/501,909, filed Oct. 14, 2021 Final Office Action dated Aug. 5, 2024.

U.S. Appl. No. 17/501,909, filed Oct. 14, 2021 Final Office Action dated Nov. 21, 2023.

U.S. Appl. No. 17/501,909, filed Oct. 14, 2021 Non-Final Office Action dated Jun. 6, 2023.

U.S. Appl. No. 17/501,909, filed Oct. 14, 2021 Non-Final Office Action dated Mar. 21, 2024.

U.S. Appl. No. 17/501,909, filed Oct. 14, 2021 Restriction Requirement dated Feb. 1, 2023.

U.S. Appl. No. 17/832,389, filed Jun. 3, 2022 Advisory Action dated Apr. 4, 2024.

U.S. Appl. No. 17/832,389, filed Jun. 3, 2022 Final Office Action dated Jan. 25, 2024.

U.S. Appl. No. 17/832,389, filed Jun. 3, 2022 Non-Final Office Action dated Oct. 6, 2023.

U.S. Appl. No. 17/832,389, filed Jun. 3, 2022 Notice of Allowance dated May 15, 2024.

U.S. Appl. No. 17/832,389, filed Jun. 3, 2022 Restriction Requirement dated Jul. 13, 2023.

U.S. Appl. No. 17/861,031, filed Jul. 8, 2022 Advisory Action dated Jun. 7, 2024.

U.S. Appl. No. 17/861,031, filed Jul. 8, 2022 Final Office Action dated Mar. 15, 2024.

U.S. Appl. No. 17/861,031, filed Jul. 8, 2022 Non-Final Office Action dated Sep. 14, 2023.

U.S. Appl. No. 17/861,031, filed Jul. 8, 2022 Notice of Allowance dated Jul. 3, 2024.

U.S. Appl. No. 17/888,359, filed Aug. 15, 2022 Restriction Requirement dated Sep. 5, 2024.

U.S. Appl. No. 18/385,101, filed Oct. 30, 2023 Notice of Allowance dated Aug. 20, 2024.

William F Garrett et al: "Real-time incremental visualization of dynamic ultrasound vols. using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

PCT/US2024/039922 filed Jul. 26, 2024 International Search Report and Written Opinion dated Jan. 9, 2025.

U.S. Appl. No. 17/478,754, filed Sep. 17, 2021 Non-Final Office Action dated Dec. 30, 2024.

U.S. Appl. No. 17/501,909, filed Oct. 14, 2021 Notice of Allowance dated Sep. 25, 2024.

U.S. Appl. No. 17/888,359, filed Aug. 15, 2022 Non-Final Office Action dated Feb. 12, 2025.

Manuel Birlo et al: "Utility of Optical See-Through Head Mounted Displays in Augmented Reality-Assisted Surgery: A systematic review", arxiv.org, Cornell University Library, 201 Olin Library Cornell University Ithaca, NY 14853, Feb. 8, 2022 (Feb. 8, 2022), XP091157128, DOI: 10.1016/J.MEDIA.2022.102361 Section 8.5, section 8.2.

PCT/US2025/027390 filed May 1, 2025 International Search Report and Written Opinion dated Jul. 29, 2025.

U.S. Appl. No. 17/478,754, filed Sep. 17, 2021 Advisory Action dated Jun. 24, 2025.

U.S. Appl. No. 17/478,754, filed Sep. 17, 2021 Final Office Action dated Apr. 11, 2025.

U.S. Appl. No. 17/478,754, filed Sep. 17, 2021 Notice of Allowance dated Aug. 14, 2025.

U.S. Appl. No. 17/888,359, filed Aug. 15, 2022 Advisory Action dated Sep. 3, 2025.

U.S. Appl. No. 17/888,359, filed Aug. 15, 2022 Final Office Action dated Jun. 18, 2025.

U.S. Appl. No. 17/888,359, filed Aug. 15, 2022 Notice of Allowance dated Oct. 21, 2025.

U.S. Appl. No. 17/890,148, filed Aug. 17, 2022 Non-Final Office Action dated Sep. 9, 2025.

U.S. Appl. No. 18/652,728, filed May 1, 2024 Non-Final Office Action dated Oct. 1, 2025.

U.S. Appl. No. 18/936,364, filed Nov. 4, 2024 Non-Final Office Action dated Feb. 5, 2025.

(56)          References Cited

OTHER PUBLICATIONS

U.S. Appl. No. 17/890,148, filed Aug. 17, 2022 Final Office Action dated Jan. 29, 2026.
U.S. Appl. No. 18/652,728, filed May 1, 2024 Final Office Action dated Apr. 3, 2026.
U.S. Appl. No. 18/786,361, filed Jul. 26, 2024 Non-Final Office Action dated Jan. 28, 2026.
U.S. Appl. No. 18/936,364, filed Nov. 4, 2024 Notice of Allowance dated Mar. 3, 2026.
U.S. Appl. No. 19/019,042, filed Jan. 13, 2025 Notice of Allowance dated Feb. 4, 2026.
U.S. Appl. No. 19/043,025, filed Jan. 31, 2025 Non-Final Office Action dated Apr. 7, 2026.

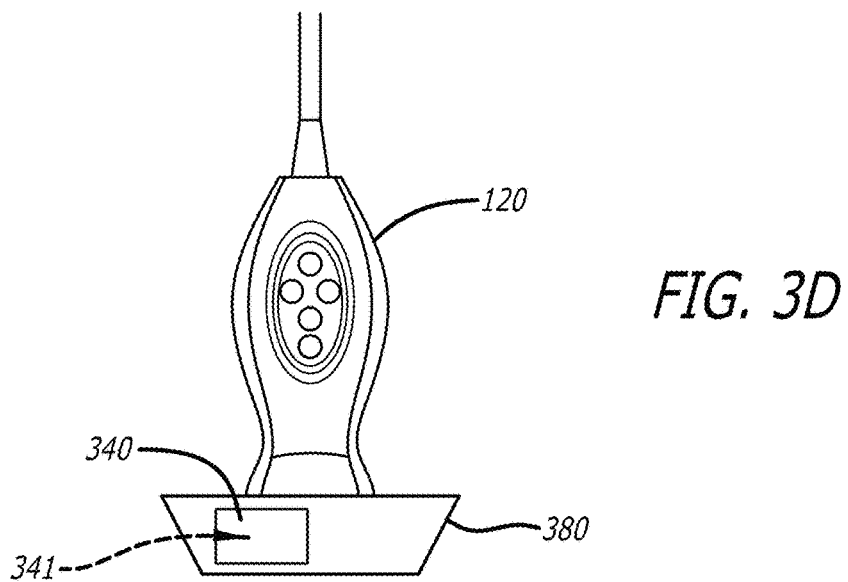
*FIG. 3D*
*FIG. 3E*
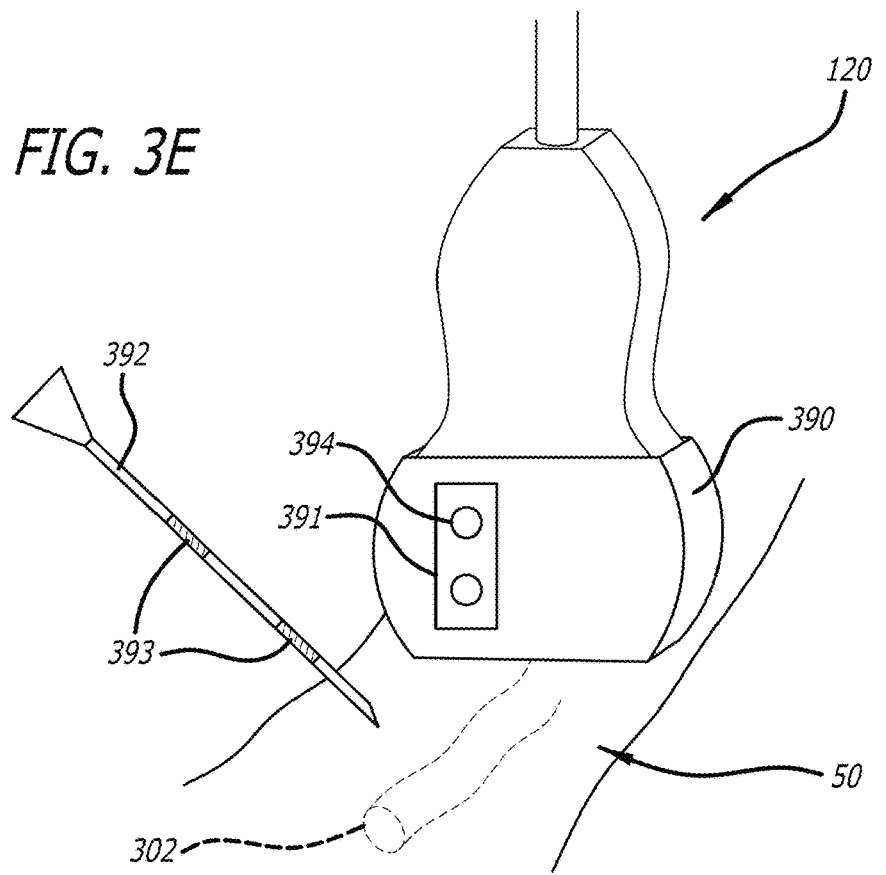

FIG. 4A
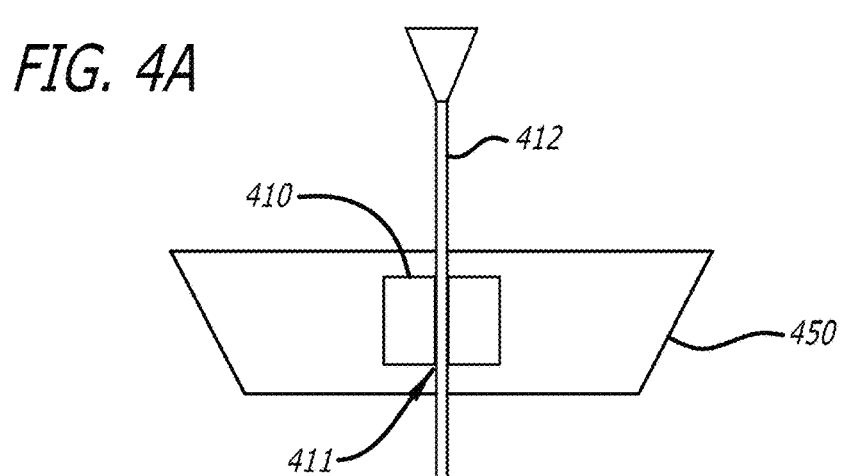
FIG. 4B
FIG. 4C
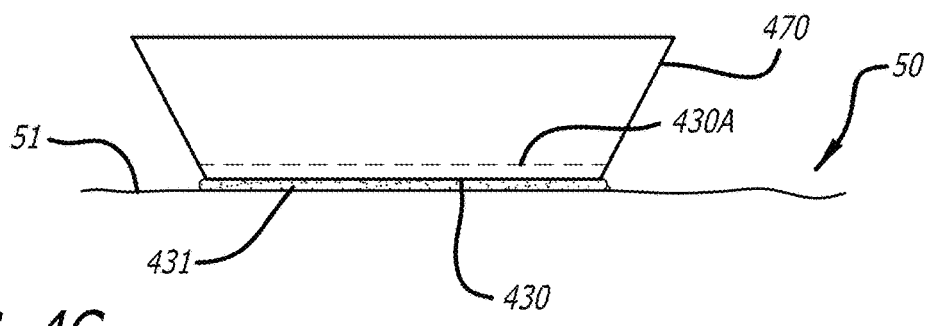

ULTRASOUND PROBE WITH SMART ACCESSORY

PRIORITY

This application is a continuation of U.S. patent application Ser. No. 17/832,389, filed Jun. 3, 2022, now U.S. Pat. No. 12,102,481, which is incorporated by reference in its entirety into this application.

BACKGROUND

Obtaining ultrasound images may be employed during a various medical procedures. Ultrasound systems and the associated ultrasound probes may be combined with a wide variety other medical devices and systems to enhance the performance of the medical procedures and reduce patient risk. However, the modification of the ultrasound systems or probes to accommodate integrated use with the other medical devices can be costly and logically complex. Systems and devices disclosed herein address the forgoing.

SUMMARY

Briefly summarized, disclosed herein is an ultrasound system that includes an ultrasound probe and an accessory attached to the ultrasound probe, where data is exchanged between the ultrasound probe and the accessory via a communication interface, and/or where the ultrasound probe supplies electrical power to the accessory via a power interface.

In some embodiments, the accessory is configured to selectively attach to and detach from the ultrasound probe.

In some embodiments, the accessory is coupled with the ultrasound probe across a medical procedural barrier.

In some embodiments, the ultrasound system further includes the medical procedural barrier, where the medical procedural barrier includes a sheath covering the ultrasound probe.

In some embodiments, the power interface includes electrical contacts, a magnetic field configured to transfer electrical power to the accessory, or a combination of the electrical contacts and the magnetic field.

In some embodiments, the communication interface includes a wireless connection between the ultrasound probe and the accessory.

In some embodiments, the wireless connection facilitates obtaining accessory identification data from an RFID chip of the accessory.

In some embodiments, the communication interface includes a fiber optic interface such that data is optically exchanged between the ultrasound probe and the accessory.

In some embodiments, the accessory is configured to obtain input data via a number of accessory devices, where the number of accessory devices includes one or more of: an operator interface including buttons, a joystick, or a scroll wheel; a fingerprint scanner; a microphone; an infrared receiver; an RFID reader; a scanner; or a camera.

In some embodiments, the accessory includes an optical fiber system including an optical fiber having a number of sensors disposed along a length of the optical fiber, and the data includes one or more of: doppler data related to fluid or tissue motion adjacent the optical fiber; an image acquired by the optical fiber; a shape or strain of the optical fiber; a motion of at least a portion of the optical fiber.

In some embodiments, the accessory includes an orientation monitoring system configured to determine an orientation of the ultrasound probe, where the orientation monitoring system includes one or more of an inertial measurement unit (IMU) or a gyroscope, and the data includes an orientation of the ultrasound probe.

In some embodiments, the accessory includes a magnetic tracking system configured to track a location and/or an orientation of a needle, and the data includes the location and/or an orientation of the elongate medical device with respect to the ultrasound probe.

In some embodiments, the accessory includes a bio-impedance system configured to determine an impedance of a substance adjacent an elongate medical device of the impedance system when the elongate medical device is inserted within the patient, and the data includes a determined impedance of the substance.

In some embodiments, the accessory includes an electrical signal monitoring system, where the electrical signal monitoring system includes an electrode disposed at a distal tip of the elongate medical device, where the electrode is configured to electrically couple with a patient when the elongate medical device is inserted within the patient, and where the data includes an electrical signal emanating from the patient.

In some embodiments, the accessory is configured to provide output via one or more of: a number of light indicators; a light projector; an audio transducer; a haptic transducer; a writing to an RFID chip; electrical signals; or fiber optic signals.

In some embodiments, the ultrasound system is configured to (i) identify one or more blood vessels within an ultrasound image and (ii) determine a location of the one or more blood vessels with respect to the ultrasound probe. In such embodiments, the ultrasound system includes the one or more light indicators and the one or more light indicators are configured to indicate the location of the one or more blood vessels.

In some embodiments, the ultrasound system is configured to (i) identify one or more blood vessels within an ultrasound image and (ii) determine a location of the one or more blood vessels with respect to the ultrasound probe. In such embodiments, the ultrasound system includes the projected light, where the projected light includes an indicium projected onto the patient, that indicates an insertion site for a needle.

In some embodiments, the accessory further includes one or more of: a needle guide; a triphalangeal support structure; a medical procedural barrier control mechanism; or an acoustically transparent cap.

In some embodiments, the accessory includes an output portal configured to provide data and/or power to an external device, where the output portal includes one or more of an electrical interface, a magnetic field interface, or an optical interface.

Also disclosed herein is an ultrasound probe accessory that, according to some embodiments, includes an accessory housing configured for selective attachment to and detachment from an ultrasound probe, and a console disposed within the housing. The console includes one or more processors and a non-transitory computer-readable storage medium having logic stored thereon that when executed by the one or more processors governs operation of the accessory to enhance functionality of the ultrasound probe. In such embodiments, the accessory is configured to receive electrical power from the ultrasound probe and/or exchange data with the ultrasound probe.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 3D is an illustration of an accessory including a probe orientation monitoring system, in accordance with some embodiments;

FIG. 3E is an illustration of an accessory including a needle tracking system, in accordance with some embodiments;

FIG. 4A is an illustration of an accessory including a needle guide, in accordance with some embodiments;

FIG. 4B is an illustration of an accessory including a triphalangeal support structure, in accordance with some embodiments; and FIG. 4C is an illustration of an accessory including an acoustically transparent cap, in accordance with some embodiments.

DETAILED DESCRIPTION

Figure 1:
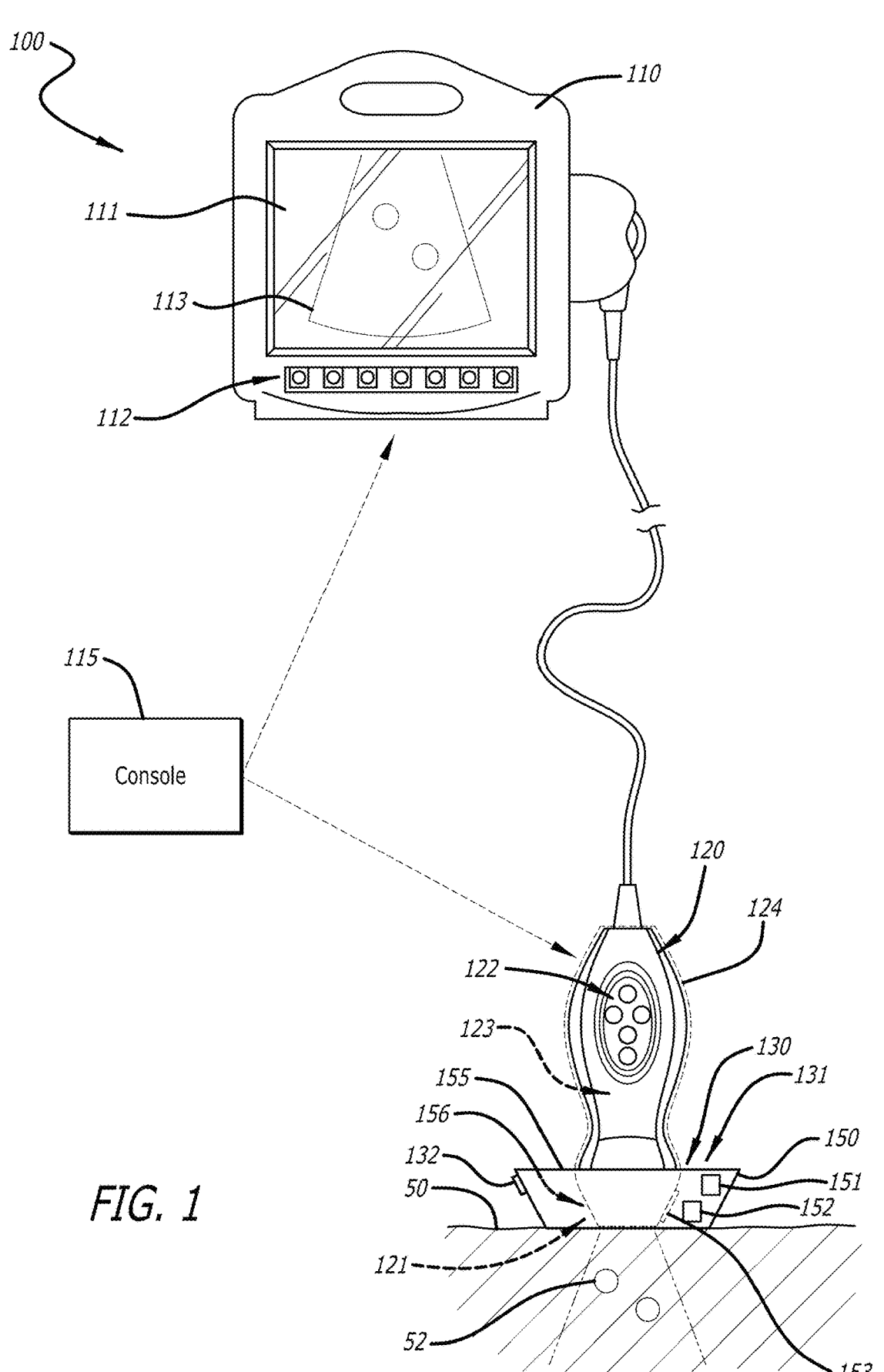
FIG. 1 is an illustration of an ultrasound imaging system including an accessory in use with a patient, in accordance with some embodiments.

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a needle or catheter placed within the body of a patient is considered a distal end of the needle or catheter, while the needle or catheter end remaining outside the body is a proximal end of the needle or catheter. Also, the words "including," "has," and "having," as used herein, including the claims, shall have the same meaning as the word "comprising."

The phrases "connected to," or "coupled with," and "in communication with" refer to any form of interaction between two or more entities, including but not limited to mechanical, electrical, magnetic, electromagnetic, fluid, wireless, and optical interaction. Two components may be physically coupled with each other even though they are not in direct contact with each other. For example, two components may be physically coupled with each other through an intermediate component.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

FIG. 1 illustrates an ultrasound imaging system (system) 100 in use with a patient 50. The system 100 is generally configured for ultrasonically imaging a target area of the patient 50. The system 100 may be configured to facilitate the placement of a medical device (e.g., a guidewire, a catheter, a needle, or the like) within a patient vasculature. In some embodiments, the system 100 may be configured to facilitate defining a vascular access pathway for the medical device, such as via the insertion of a needle, for example. In some embodiments, the system 100 may further facilitate the positioning and/or orienting of the needle so that the needle may be accurately inserted into a target blood vessel.

The system 100 generally includes a display module 110, an ultrasound probe (probe) 120, and a console 115. The display module 110 includes a display 111. The display 111 and the probe 120 each include one or more user input controls 112, 122, respectively. The console 115 includes a number of console components (not shown) that govern the operation of the system 100. The console components may include inter alia one or more processors and memory (e.g., non-volatile memory or non-transitory, computer-readable storage medium) having logic stored thereon. Any portion of the console 115 may be included in the display module 110 and/or the probe 120. Briefly, the probe 120 is configured to (i) transmit ultrasonic signals from a head portion 121 thereof into a portion of a patient body 50 and (ii) receive the ultrasonic signals after reflection by internal structures of the patient body. The system 100 processes the reflected ultrasonic signals for depiction on the display 111. The system 100 may also be configured to (i) identify one or more blood vessels 52 within an ultrasound image 113 and (ii) determine a location of the one or more blood vessels 52 with respect to the probe 120.

The system 100 further includes an accessory 150 coupled with the probe 120. The accessory 150 includes a housing 155 configured to selectively attach to and detach from the probe 120. The accessory 150 is a smart device, i.e., the accessory 150 includes a console 156 disposed within the housing 155 that may include one or more processors, and memory (e.g., non-transitory computer-readable storage medium) having logic stored thereon that governs the operation of the accessory 150. The accessory 150 is one of a number (e.g., 2, 3, 4, 5, 6 or more) of optional accessories that may be coupled with the probe 120 and configured to enhance functionality of the probe 120 or the system 100 as a whole.

The accessory 150 may be configured to exchange data with the probe 120 via a communication interface 130. The communication interface 130 may include a number of a communication mechanisms either individually or in combination between the accessory 150 and the probe 120. The communication mechanisms may include an electrical connection, a fiber optical coupling, an inductive (or magnetic field) coupling, or a wireless connection. Exemplary wireless communication modalities can include WiFi, Bluetooth, Near Field Communications (NFC), cellular Global System for Mobile Communication ("GSM"), electromagnetic (EM), radio frequency (RF), combinations thereof, or the like. The data may include any information related to the operation of the accessory 150. The data may also include identification data of the accessory 150, such as a name, a model, a serial number, and/or manufacturing date, for example.

In some embodiments, the accessory 150 may be configured to only transmit data to the probe 120, and in some embodiments the accessory 150 may be configured to only receive data from the probe 120. In further embodiments, the accessory 150 may be configured to neither transmit data to the probe 120 nor receive data from the probe 120.

In some embodiments, the probe 120 may include a radio frequency identification (RFID) reader 123 configured to obtain information from the accessory 150 including an identification of the accessory 150. As discussed above, the accessory 150 may be one of a number of accessories and a such each accessory may include a unique identification. By way of example, in use, the RFID reader 123 may obtain the unique identification of the accessory 150 from an RFID chip of the accessory.

The accessory 150 may receive electrical power from the probe 120 via a power interface 131. The power interface 131 may include an electrical connection, or an inductive (or magnetic field) coupling. In some embodiments, the accessory 150 may include a power source (e.g., battery) to augment the electrical power received from the probe 120. In some embodiments, the accessory 150 may include a power source (e.g., battery) as an alternative to receiving electrical power from the probe 120, and as such, the accessory 150 may be configured to not receive electrical power from the probe 120.

In some embodiments, the accessory 150 is coupled with the probe 120 across a medical procedural barrier 124 to define a sterile barrier between the probe 120 and the patient. In some embodiments, the medical procedural barrier 124 includes a sheath that covers the probe 120. As such, the communication interface 130 and the power interface 131 are configured to operate across the medical procedural barrier 124. In some embodiments, the system 100 may include the medical procedural barrier 124.

In some embodiments, the system 100 may include a barrier control mechanism 153. The barrier control mechanism 153 may be configured to isolate or control a portion of the medical procedural barrier 124 disposed between the probe 120 and the accessory 150 so that an electrical connection may breach the medical procedural barrier 124 while maintaining the functionality of the medical procedural barrier 124. Defining the electrical connection may include piercing the medical procedural barrier 124 with one or more electrical pins of blades (not shown).

In some embodiments, the accessory 150 includes an output portal 132 configured to provide data and/or power to an external device. The output portal 132 may include an electrical connection interface to enable to the accessory 150 to electrically provide the data and/or the power to the external device. Alternatively, or in addition to the electrical connection interface, the output portal 132 may include an inductive (or magnetic field) interface to provide the data and/or the power to the external device. The output portal 132 may also include an optical interface to optically provide the data to the external device.

The accessory 150 may be configured to obtain input data via one or more of a number of optional accessory input devices 151. The input devices 151 may include an operator interface having buttons, a joystick, or a scroll wheel for manually inputting data, or adjusting settings of the accessory 150. The input devices 151 may include a fingerprint scanner to obtain an identification of a clinician or the patient 50. The input devices 151 may include a microphone to obtain and/or record audio information, where the audio information may include clinician or patient speech, audio output (e.g., alarms) of other medical equipment, or any other audible sounds during use of the system 100. The input devices 151 may include an infrared (IR) receiver for receiving input via an IR or near IR connection.

The input devices 151 may include an RFID reader; a scanner; and/or camera for obtaining and/or logging data from any suitable source, such as separate medical device, a medical fluid container, a clinician ID badge, or a patient ID bracelet, for example.

The accessory 150 may be configured to provide output, such as output data to the clinician. The output may be provided via one or more output devices 152, such as an audio transducer and/or a haptic transducer. The output may also be provided via data writings to the RFID chip, electrical signals, or fiber optic signals. In some embodiments, the accessory 150 may include the audio transducer to sound an alarm or other audible notification. For example, the accessory 150 may provide an event notification via the audio transducer for various events during a procedure, such as a cannulation of the target blood vessel, a vein/artery confirmation, or a deviation of a needle from vasculature access pathway, for example. Similarly, as the probe 120 is hand-held, the accessory 150 may cause a vibration of the probe 120 via the haptic transducer in response to various procedural events. In some embodiments, the accessory 150 may generate a data packet of procedural events and send the data packet to the probe 120 via the communication interface 130 or to an external device via the output portal 132.

FIGS. 2A-4C illustrates various accessory embodiments. It is noted that any subset of the accessory embodiments of FIGS. 2A-4C may be combined to define additional accessory embodiments.

Figure 2A:
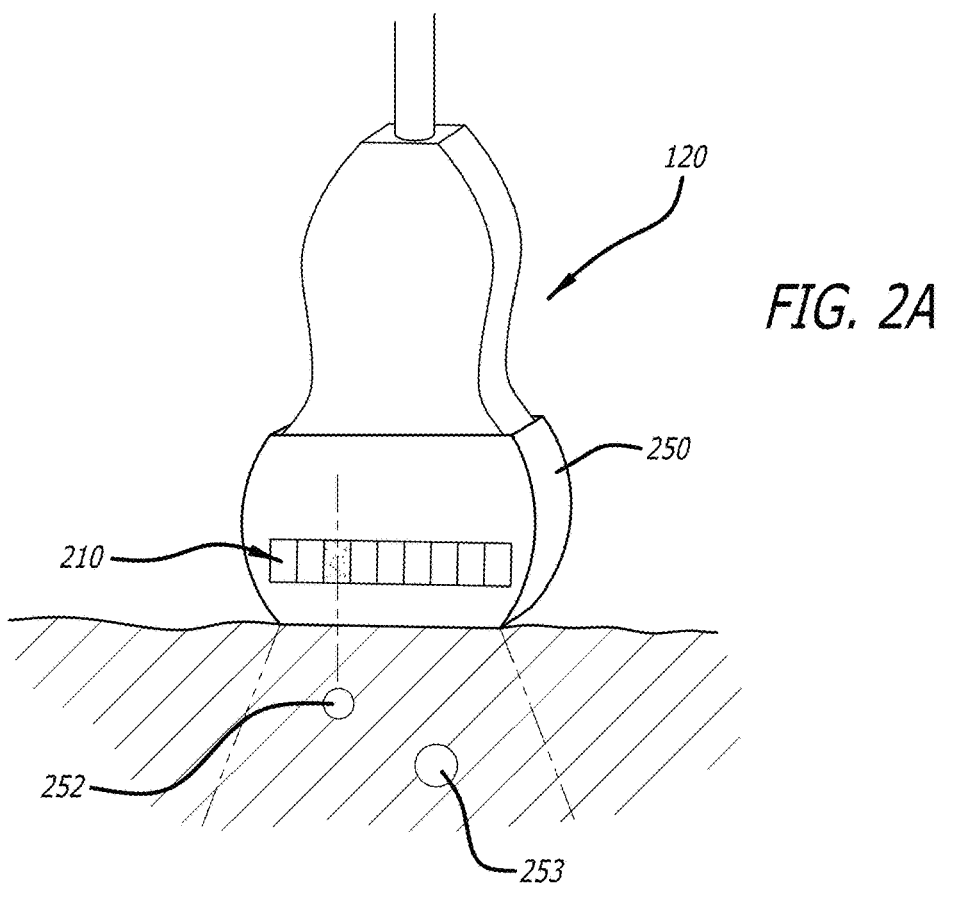
FIG. 2A is an illustration of an ultrasound probe of FIG. 1 with an attached accessory having a number of light indicators, in accordance with some embodiments.

FIG. 2A illustrates an accessory 250 attached to the probe 120, where the accessory 250 may in some respects resemble the components and functionality of the accessory 150. The accessory 250 includes a number of light indicators 210 arranged to indicate a location in relation to the probe 120. The location may include center location of the probe 120 or location of a target blood vessel such as the vein 252 in with respect to the probe 120, for example. In some embodiments, the light indicators 210 may be configured indicate a target blood vessel, such as the vein 252 in accordance with image data received from the probe 120. Still in other embodiments, the light indicators 210 may be configured differentiate one blood vessel from another blood vessel. For example, the light indicators 210 may be configured differentiate the vein 252 from an artery 253. In some embodiments, the accessory 250 may be configured to not transmit data to the probe 120.

Figure 2B:
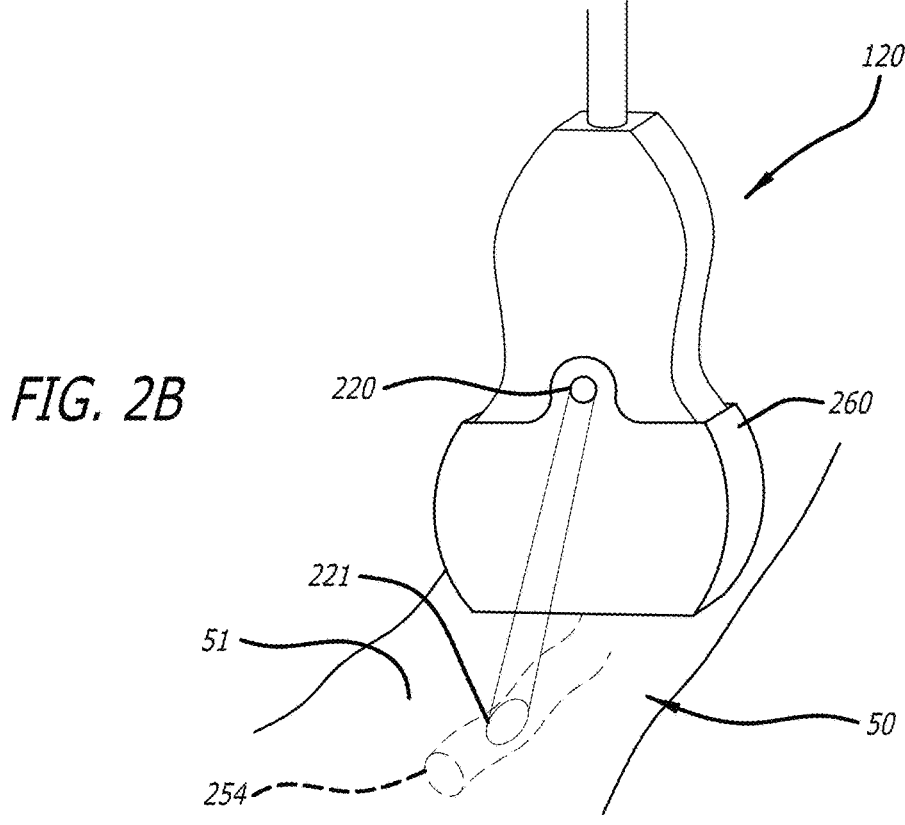
FIG. 2B is an illustration of the ultrasound probe of FIG. 1 with an attached accessory having a light projector, in accordance with some embodiments.

FIG. 2B illustrates an accessory 260 attached to the probe 120, where the accessory 260 may in some respects resemble the components and functionality of the accessory 150. The accessory 260 includes a light projector 220 configured to display images, shapes, indicia, colors, or the like onto the skin surface 51 of the patient 50. For example, the light projector 220 may project an indicium 221 on the skin surface 51 of the patient 50 indicating a calculated (or otherwise determined) insertion site 221 for the target blood vessel 254 in accordance with image data received from the probe 120. Similar to the light indicators 210, the light projector 220 may be configured to differentiate one blood vessel from another blood vessel. For example, the light projector 220 may be configured differentiate a vein from an artery. In some embodiments, the light projector 220 may project an indicium, such as an "A", for example, adjacent an artery and a "V" adjacent a vein. The light projector 220 may indicate an artery versus a vein in other ways, such as projecting a color over a projected image of the blood vessel. As may be appreciated by one of ordinary skill, many other suitable ways of differentiating a vein from an artery or otherwise identifying a blood vessel via the projector 220 may be employed, which other suitable ways are disclosed herein. In some embodiments, the accessory 260 may be configured to not transmit data to the probe 120.

Figure 3A:
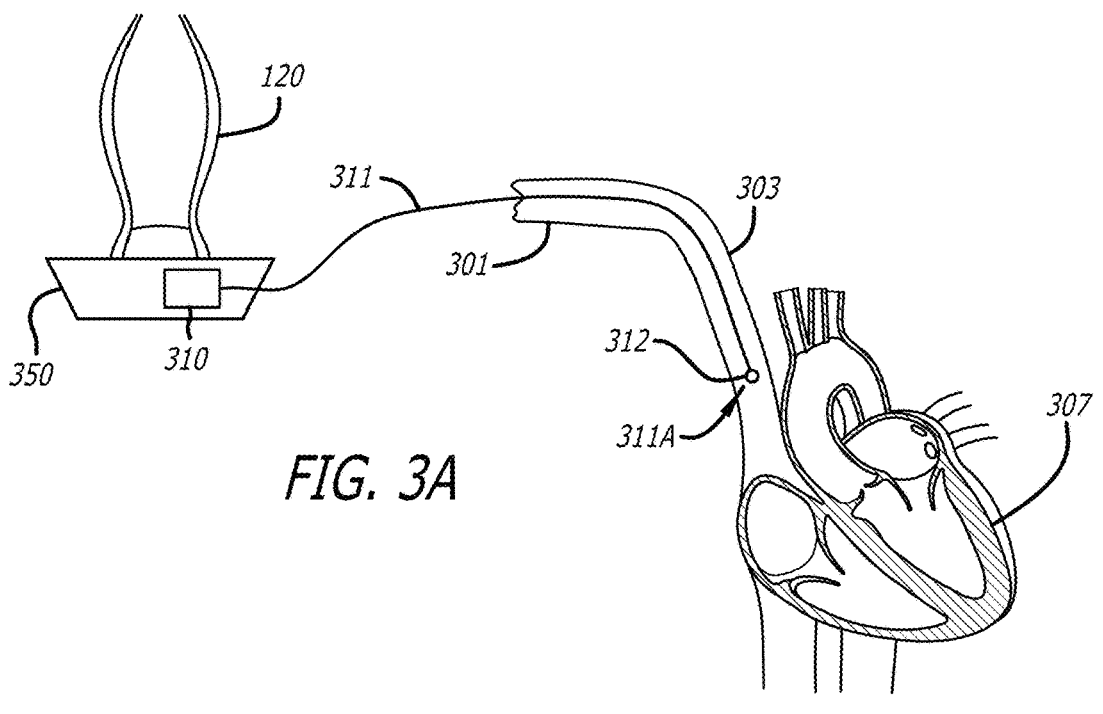
FIG. 3A is an illustration of an accessory including an electrical signal monitoring system, in accordance with some embodiments.

FIG. 3A illustrates a distal portion of the probe 120 having the accessory 350 attached thereto, where the accessory 350 may in some respects resemble the components and functionality of the accessory 150. The accessory 350 includes an electrical signal monitoring system 310 that includes an elongate medical device 311 configured for advancement along a vasculature 301 of the patient, such as the superior vena cava 303 entering the heart 307 of the patient, for example. The elongate medical device 311 includes an electrode 312 at a distal end 311A, where the electrode 312 is configured to obtain an electrical signal from the patient 50 such as an electro-cardiogram (ECG) signal, for example. As such, the system 100 may be configured to obtain an ECG signal or any other electrical signal emanating from or otherwise present within the patient.

Figure 3B:
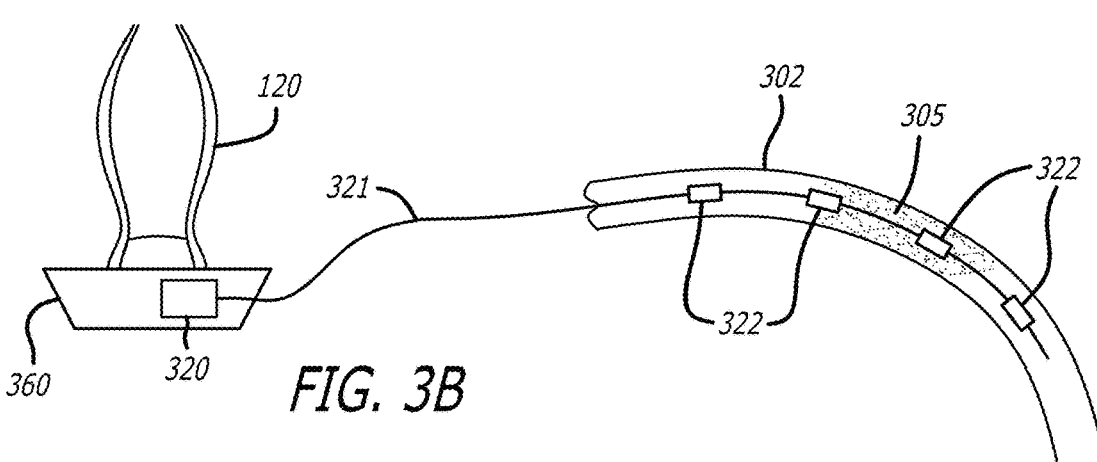
FIG. 3B is an illustration of an accessory including a fiber optic system, in accordance with some embodiments.

FIG. 3B illustrates a distal portion of the probe 120 having the accessory 360 attached thereto, where the accessory 360 may in some respects resemble the components and functionality of the accessory 150. The accessory 360 includes a fiber optic system 320 that includes a multi-core optical fiber 321 having a number of sensors (e.g., Fiber Bragg Gratings) 322 disposed along the optical fiber 321. The optical fiber 321 may be configured for advancement along a blood vessel 302 of the patient 50 so that the fiber optic system 320 may acquire data related to the blood vessel 302. In some embodiments, fiber optic system 320 may determine a fluid (e.g., blood 305) or tissue motion adjacent the optical fiber 321 via the doppler effect. The fiber optic system 320 may further acquire data related to a strain, a shape, or a motion of at least a portion of the optical fiber 321 when the optical fiber 321 is advanced along the blood vessel 302. The fiber optic system 320 may also obtain images via the optical fiber 321, such as an image of an interior of a blood vessel, for example. During use, the fiber optic system 320 may provide data to the system 100 related to blood flow, shape or strain of the optical fiber 321, a motion of the optical fiber 321, and/or an image obtained by the optical fiber 321.

Figure 3C:
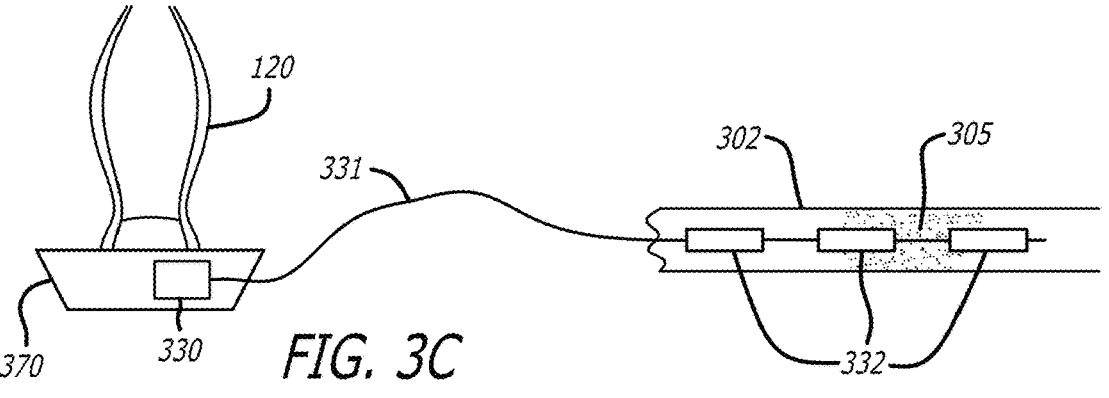
FIG. 3C is an illustration of an accessory including a bio-impedance system, in accordance with some embodiments.

FIG. 3C illustrates a distal portion of the probe 120 having the accessory 370 attached thereto, where the accessory 370 may in some respects resemble the components and functionality of the accessory 150. The accessory 370 includes an impedance system 330 having an elongate medical device 331 (e.g., a catheter, a guidewire, a needle, or a stylet) that may be inserted into the patient, such as advancement along a blood vessel 302, for example. The elongate medical device 331 includes two or more electrodes 332 distributed along the elongate medical device 331. The two or more electrodes 332 are configured to obtain an electrical impedance of a bodily substance, such as the blood 305 within the blood vessel 302, for example. In some embodiments, the elongate medical device 331 may be configured for insertion into body tissue so that the two or more electrodes 332 may obtain an electrical bio-impedance of the tissue. During use, the impedance system 330 may provide bio-impedance data to the system 100.

FIG. 3D illustrates a distal portion of the probe 120 having the accessory 380 attached thereto, where the accessory 380 may in some respects resemble the components and functionality of the accessory 150. The accessory 380 includes a probe orientation monitoring system 340. The probe orientation monitoring system 340 includes a gyroscope and/or an inertia measurement unit (IMU) 341 to determine the orientation and/or position of the probe 120. In some instances, the clinician may reposition the probe 120 during a procedure. As such, the probe orientation monitoring system 340 is configured to monitor and determine the orientation and/or position of the probe 120. In some embodiments, the probe orientation monitoring system 340 may determine the orientation/position or a shift in the orientation/position of the probe 120 during use. The accessory 380 may further provide data to the system 100 pertaining to the orientation/position or a shift in the orientation/position of the probe 120.

FIG. 3E illustrates a distal portion of the probe 120 having the accessory 390 attached thereto, where the accessory 390 may in some respects resemble the components and functionality of the accessory 150. The accessory 390 includes a needle tracking system 391 configured to track (e.g., magnetically track) the orientation and/or position of a needle 392 with respect to the probe 120 during use. In some embodiments, the needle 392 may include a number of magnetic elements 393 and the needle tracking system 391 may include a number of magnetic sensors 394. A Medical device tracking and guidance system is described for various instruments, including needles, in U.S. Pat. No. 9,521,961 titled "Systems and Methods for Guiding a Medical Instrument" filed on Dec. 23, 2011, which is included herein by reference in its entirety. The needle tracking system 391 provides needle tracking data to the system 100.

FIG. 4A illustrates the accessory 450, where the accessory 390 may in some respects resemble the components and functionality of the accessory 150. The accessory 450 includes a needle guide 410 attached thereto. The needle guide 410 includes a channel 411 configured for receiving a needle 412 therein such that the needle guide 410 defines a lateral position and an orientation of the needle 412 with respect to the accessory 450 (i.e., the probe 120) during use. In some embodiments, the accessory 450 may alternatively include a needle guide connector (not shown) configured for selective attachment to and detachment from the needle guide 410. As the accessory 450 may be a passive device, the accessory 450 may be configured to neither exchange data with nor receive electrical power from the probe 120.

FIG. 4B illustrates an accessory 460 that may in some respects resemble the components and functionality of the accessory 150. The accessory 460 includes triphalangeal stabilization structure 420 (e.g., a tripod structure) having three support members (legs) 421-423 extending between the accessory 450 and the skin surface 51 of the patient 50. The triphalangeal stabilization structure 420 is configured to enhance the stabilization of the probe 120 when the probe 120 is placed on the patient. As the accessory 460 may be a passive device, the accessory 460 may be configured to neither exchange data with nor receive electrical power from the probe 120.

FIG. 4C illustrates an accessory 470 that may in some respects resemble the components and functionality of the accessory 150. The accessory 470 includes a lens cap 430 configured for disposition between the probe 120 and the skin surface 51, where the lens portion 430A of the lens cap 430 is ultrasonically transparent. In some embodiments, the lens cap 430 includes a gel 431 to enhance an ultrasonic coupling of the probe 120 with the skin surface 51. As the accessory 470 may be a passive device, the accessory 470 may be configured to neither exchange data with nor receive electrical power from the probe 120.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A method of using an ultrasound system, the ultrasound system including an ultrasound probe and an accessory, the method comprising:
   coupling the ultrasound probe to the accessory across a medical procedural barrier, the accessory comprising a fiber optic system including an optical fiber having a plurality of sensors disposed along a length thereof;
   advancing the optical fiber along a blood vessel of a patient; and
   optically exchanging data between the ultrasound probe and the accessory via a communication interface including a fiber-optical coupling mechanism, the data selected from the group consisting of doppler data related to fluid or tissue motion adjacent the optical fiber, an image acquired by the optical fiber, a shape or strain of the optical fiber, a motion of the optical fiber, and combinations thereof.

2. The method according to claim 1, further comprising detaching the ultrasound probe from the accessory following use.

3. The method according to claim 1, further comprising transferring electrical power from the ultrasound probe to the accessory via a power interface.

4. The method according to claim 3, wherein transferring the electrical power includes utilizing electrical contacts and/or a magnetic field associated with the power interface.

5. The method according to claim 1, wherein the communication interface further comprises a wireless connection.

6. The method according to claim 5, further comprising obtaining accessory identification data from an RFID chip of the accessory.

7. The method according to claim 1, further comprising providing input data to the accessory via an accessory input device selected from the group consisting of an operator interface including buttons, a joystick, a scroll wheel, a fingerprint scanner, a microphone, an IR receiver, an RFID reader, a scanner, a camera, and combinations thereof.

8. The method according to claim 1, wherein the accessory includes an orientation monitoring system including one or more of an inertial measurement unit (IMU) or a gyroscope, further comprising determining an orientation of the ultrasound probe.

9. The method according to claim 1, wherein the accessory includes a magnetic tracking system, further comprising tracking one or more of a location or an orientation of a needle.

10. The method according to claim 1, wherein the accessory includes a bio-impedance system, further comprising determining an impedance of a substance adjacent a medical device of the bio-impedance system when the medical device is inserted in the blood vessel.

11. The method according to claim 1, wherein the accessory includes an electrical signal monitoring system comprising an electrode disposed at a distal tip of a medical device, further comprising electrically coupling the electrode with the patient when the medical device is inserted in the blood vessel.

12. The method according to claim 1, wherein the accessory includes an output selected from the group consisting of a plurality of light indicators, a light projector, an audio transducer, a haptic transducer, a writing to an RFID chip, electrical signals, fiber optic signals, and combinations thereof.

13. The method according to claim 1, further comprising identifying one or more blood vessels within an ultrasound image and determining a location of the one or more blood vessels with respect to the ultrasound probe.

14. The method according to claim 13, wherein the ultrasound system includes one or more light indicators, further comprising indicating the location of the one or more blood vessels with respect to the ultrasound probe via the one or more light indicators.

15. The method according to claim 13, wherein the ultrasound system includes a light projector, further comprising projecting an indicium onto the patient, the indicium indicating an insertion site for a needle to access the blood vessel.

16. The method according to claim 1, wherein the accessory further includes one or more of a needle guide, a triphalangeal support structure, a medical procedural barrier control mechanism, or an acoustically transparent cap.

17. The method according to claim 1, wherein the accessory further includes an output portal including one or more of an electrical interface, a magnetic field interface, or an optical interface, further comprising providing data and/or power to an external device via the output portal.

* * * * *